United States Patent [19]

Skoldinov et al.

[11] 4,230,856
[45] Oct. 28, 1980

[54] 1,2,3,4-TETRAHYDROPYRROLO-[1,2-A]-PYRAZINE

[76] Inventors: Alexandr P. Skoldinov, ulitsa Alabiana, 3, kv. 60; Arkady M. Likhosherstov, ulitsa Smolnaya, 33, kv. 107; Vitaly P. Peresada, ulitsa Astradamskaya, 8, kv. 31, all of Moscow, U.S.S.R.

[21] Appl. No.: 927,995

[22] Filed: Jul. 26, 1978

[51] Int. Cl.² ............... A61K 31/495; C07D 487/04
[52] U.S. Cl. .................................. 544/349; 424/250
[58] Field of Search ........................................ 544/349

[56] References Cited

U.S. PATENT DOCUMENTS

| | | | |
|---|---|---|---|
| 3,281,423 | 10/1966 | Rogers et al. | 544/349 |
| 3,531,485 | 9/1970 | Freed | 544/349 |
| 3,998,820 | 12/1976 | Likhosherstov et al. | |
| 4,044,015 | 8/1977 | Kuhla | 544/349 |

FOREIGN PATENT DOCUMENTS

| | | | |
|---|---|---|---|
| 50-88093 | 7/1975 | Japan | 544/349 |
| 237153 | 6/1969 | U.S.S.R. | 544/349 |

OTHER PUBLICATIONS

Rayevskii, et al., "Jour. Pharm. Chem.", (U.S.S.R.), vol. 10, 1976, pp. 55–58.
Freed, et al., "J. Org. Chem.", vol. 25, 1960, pp. 2108–2113.
Nazarova, "J. Pharm. Chem.", (U.S.S.R.), vol. 10, No. 1, 1976, pp. 88–92.
Likhosherstov, et al., "Zhur. Org. Khimii", vol. VI, No. 8, 1970, pp. 1731–1734.
Ponomarev, et al., "Doklady Akademii Nauk" (U.S.S.R.), vol. 148, No. 4, 1963, pp. 860–862.

*Primary Examiner*—Donald G. Daus
*Assistant Examiner*—James H. Turnipseed
*Attorney, Agent, or Firm*—Robert E. Burns; Emmanuel J. Lobato; Bruce L. Adams

[57] ABSTRACT

1,2,3,4-Tetrahydropyrrolo-[1,2-a]-pyrazine of the formula:

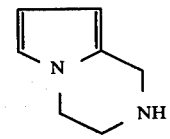

is disclosed together with a method for preparing the same which comprises reducing 3,4-dihydropyrrolo-[1,2-a]-pyrazine, in a medium of an organic solvent, by way of hydrogenation with hydrogen or complex hydrides of metals. When using hydrogen said hydrogenation is effected in the presence of a catalyst of the group of platinum. The desired product is then isolated from the reaction mixture. The resulting 1,2,3,4-tetrahydropyrrolo-[1,2-a]-pyrazine may be used as the starting product for the synthesis of physiologically active compounds such as octahydropyrrolo-[1,2-a]-pyrazine which serves as the basis for the preparation of coronary-dilating and neuroleptic compounds. The method for preparing 1,2,3,4-tetrahydropyrrolo-[1,2-a]-pyrazine is technologically simple and may be readily implemented on a commercial scale.

1 Claim, No Drawings

1,2,3,4-TETRAHYDROPYRROLO-[1,2-A]-PYRAZINE

FIELD OF THE INVENTION

The present invention relates to a novel compound 1,2,3,4-tetrahydropyrrolo-[1,2-a]-pyrazine and a method for preparing same.

Said novel compound is useful as the starting product for the synthesis of various physiologically active compounds, in particular for the synthesis of octahydropyrrolo-[1,2-a]-pyrazine which serves as the basis for the preparation of the coronary-dilating compound, 10-{β-[N-/1,4-diazabicyclo(4,3,0)-nonanyl/propionyl]}-2-chlorophenothiazine dichlorohydride and the neuroleptic compound, γ-[N-/1,4-diazabicyclo-(4,3,0)-nonanyl/]-propyl-para-fluorophenyl ketone dichlorohydride.

BACKGROUND OF THE INVENTION

In the prior art methods of synthesis of physiologically active compounds, 10-{β-[N/1,4-diazabicyclo-(4,3,0)-nonanyl/propionyl]}-2-chlorophenothiazine dichlorohydride and γ-[N-/1,4-diazabicyclo-(4,3,0)-nonanyl/]-propyl-parafluorophenyl ketone dichlorohydride use is made of octahydropyrrolo-[1,2-a]-pyrazine which, in turn, is prepared by reducing hexahydropyrrolo-[1,2-a]-pyrazin-1-one with lithium alumohydride in the medium of diethyl ether. The starting hexahydropyrrolo-[1,2-a]-pyrazin-1-one is prepared by a multistage synthesis from δ-chlorovaleric acid (cf. Likhoscherstov et al., J. Org. Chem. (USSR), volume VI, p. 1729 (1970) involving bromination of δ-chlorovaleric acid in the presence of PCl₃, esterification of the resulting product, followed by a condensation thereof with ethylenediamine. This method has the disadvantage of the necessity of using a hazardous and rarely-available lithium alumohydride, a hazardous solvent and the difficulty of preparation of the starting hexahydropyrrolo-[1,2-a]-pyrazin-1-one.

Also known in the art is a method of preparing octahydropyrrolo-[1,2-a]-pyrazine by the catalytic dehydration a furandiamine. This prior art method has the disadvantage of complicated technology with respect to the process of dehydration of N-tetrahydrofurfurylethylenediamine in a quartz tube at a temperature within the range of from 300° to 315° C. over alumina activated with zirconia. This method is difficult to implement commercially on a large scale. Another disadvantage of the method is the low yield of the desired product, i.e. about 30%.

SUMMARY OF THE INVENTION

It is an object of the present invention to provide such a novel compound, i.e. 1,2,3,4-tetrahydropyrrolo-[1,2-a]-pyrazine which, when used as the starting product, would enable the production, in a simple and efficaceous manner, of the above-mentioned physiologically active compounds.

The novel compound according to the present invention is a hitherto unknown compound, i.e. 1,2,3,4-tetrahydropyrrolo-[1,2-a]-pyrazine having the following structural formula:

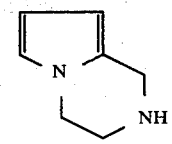

DESCRIPTION OF THE INVENTION

According to the invention 1,2,3,4-tetrahydropyrrolo-[1,2-a]-pyrazine of the above formula is prepared by reduction of the corresponding 3,4-dihydropyrrolo-[1,2-a]-pyrazine in an organic solvent by hydrogenation with hydrogen in the presence of a platinum catalyst or with a complex hydride of a metal.

1,2,3,4-Tetrahydropyrrolo-[1,2-a]-pyrazine is a colourless liquid with the amine odour and boiling point of 100°–101° C./7 mm Hg, $n_D^{20}=1.5530$. The structure of the resulting compound is proven by the data of elemental analysis of the base and salts, as well as by spectra of proton-magnetic resonance (PMR) and mass-spectrum. In the PMR spectrum there is a singlet at 1.56 m.d. (scale δ, internal reference by tetramethylsilane) corresponding to one proton of the NH-group, two triplets centered at 2.86 m.d. and 3.63 p.p.m. corresponding to four protons at $C_3$ and $C_4$ carbon atoms; a singlet at 3.8 p.p.m. corresponding to two protons at the atoms of carbon $C_1$; and three multiplets within the range of from 5.56 to 5.7 p.p.m.; 5.86–6.0 p.p.m.; 6.23–6.37 p.p.m. corresponding to three protons at carbon atoms $C_6$, $C_7$ and $C_8$. The integral curve corresponds, in toto, to ten protons and its pattern corresponds to the formula given hereinbefore for the compound according to the present invention. The individual character of the compound is proven by the gas-chromatography method and its molecular weight is determined from the data of mass-spectrography showing that M+ has m/e of 122.

In accordance with the present invention, the method for preparing 1,2,3,4-tetrahydropyrrolo-[1,2-a]-pyrazine consists in that 3,4-dihydropyrrolo-[1,2-a]-pyrazine is subjected to reduction, in a medium of an organic solvent, by way of hydrogenation with hydrogen or complex hydrides of metals; in the case of using hydrogen, said hydrogenation is effected in the presence of a catalyst pertaining to the group of platinum, followed by isolation of the desired product from the resulting reaction mixture.

As the complex hydrides of metals use may be made of various complex hydrides of metals which reduce the double bond C=N in Schiff's bases. It is preferable to use complexes readily available and widely employed for such reaction as lithium alumohydride and boronhydrides of sodium and potassium.

In effecting the reduction by way of a catalytic hydrogenation or by means of potassium boron hydride, it is advisable to use, as the organic solvent, lower aliphatic alcohols. Most preferable are methanol and ethanol. In reduction by means of lithium alumohydride it is advisable to use aliphatic ethers or cyclic ethers. Most preferable is diethyl ether.

In the method according to the present invention use may be made of the platinum group catalysts which are employed for hydrogenation of the double bond C=N in Schiff's bases. First of all, for the process according to the present invention use may be made of readily available platinum and palladium catalysts prepared by conventional techniques or platinum and palladium catalysts prepared on carriers (e.g. a platinum catalyst prepared according to Adams; palladium catalyst supported on barium sulphate).

In the method according to the present invention the double bond is reduced in the 1,2-position of 3,4-dihydropyrrolo-[1,2-a]-pyrazine with the formation of 1,2,3,4-tetrahydropyrrolo-[1,2-a]-pyrazine.

The synthesis of 1,2,3,4-tetrahydropyrrolo-[1,2-a]-pyrazine is conducted in accordance with the following scheme:

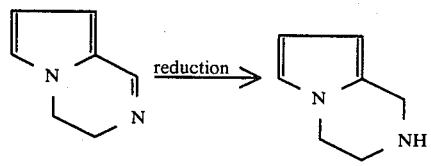

As it is seen from the structural formula of 3,4-dihydropyrrolo-[1,2-a]-pyrazine, it contains three double bonds, two of them belong to the pyrrol part of the heterocycle and the third double bond is conjugated with the pyrrol system and may be regarded as a double bond in a Schiff's base. Under the conditions of the method according to the present invention only one double bond is reduced in the position 1,2 of the heterocycle without, however, involving in reduction the double bonds of the pyrrol part of the heterocycle.

In reduction with lithium alumohydride as a solvent use is generally made of ethers.

The method according to the invention, wherein lithium alumohydride is used, proceeds quite well in diethyl ether extensively used for such purposes. In this connection, the most preferable temperature range has, as its upper limit, the boiling point of diethyl ether and, thus is 25° to 36° C.

In reduction with potassium or sodium boronhydrides, as the solvent use is generally made of lower aliphatic alcohols. Since it is advisable to use methanol and ethanol as readily available alcohols, the reduction process in these cases should be preferably carried out respectively at the boiling temperature of said solvents (i.e. within the range of from 65° to 80° C.).

The resulting 1,2,3,4-tetrahydropyrrolo-[1,2,-a]-pyrazine may be used as an intermediate product for the synthesis of physiologically active compounds.

An advantage of the use of 1,2,3,4-tetrahydropyrrolo-[1,2-a]-pyrazine as an intermediate product resides in the possibility of performing, on a commercial scale, the process of producing octahydropyrrolo-[1,2,-a]-pyrazine. Moreover, the method for preparing 1,2,3,4-tetrahydropyrrolo-[1,2-a]-pyrazine is simple in implementation, since as the starting stock for its synthesis use is made of 3,4-dihydropyrrolo-[1,2-a]-pyrazine which, in turn, is obtained from readily available furfurol.

The method for preparing 1,2,3,4-tetrahydropyrrolo-[1,2-a]-pyrazine is technologically simple and may be performed in the following manner.

The starting product, i.e. 3,4-dihydropyrrolo-[1,2-a]-pyrazine is prepared by reacting dialkylacetals or dioxalane of 2,5-dialkoxytetrahydrofurfurol with ethylenediamine in a medium of lower aliphatic acids at a temperature within the range of from 100° to 150°, followed by isolation of the desired product by conventional techniques.

The reaction proceeds according to the following scheme:

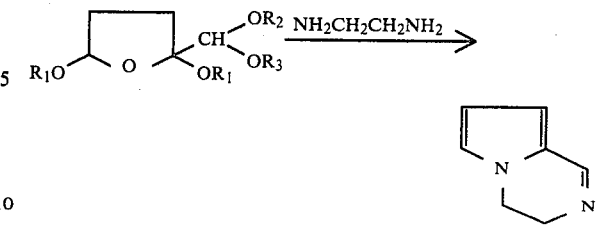

wherein $R_1=R_2=R_3=CH_3$, or $R_1=R_2=R_3=C_2H_5$, or $R_1=CH_3$, $R_2$, $R_3=-CH_2CH_2-$.

The resulting 3,4-dihydropyrrolo-[1,2-a]-pyrazine is dissolved in an organic solvent and reduced by one of the following methods.

In the case of using the method of catalytic hydrogenation, the reduction process is conducted at room temperature under atmospheric pressure in the presence of the platinum group catalysts. The process is conducted under stirring in a closed system in a solution of a lower aliphatic alcohol in the atmosphere of hydrogen. The process speed depends on the character of the catalyst employed. After absorption of the theoretical amount of hydrogen, the catalyst is filtered-off, the solvent is distilled-off from the filtrate and the desired product is purified by distillation in vacuum.

Upon reduction by means of potassium boron hydride the process is preferably performed under stirring at a temperature within the range of from 65° to 80° C. in solutions of lower aliphatic alcohols. The process speed depends on the temperature at which the process is performed. Isolation of the desired product is effected by addition of water to the reaction mixture and a subsequent extraction of the product with benzene. After distilling-off the solvent, the desired product is purified by distillation in vacuum.

In reduction by means of lithium alumohydride the process is preferably conducted under stirring at a temperature within the range of from 25° to 36° C. in a solution of diethyl ether. The process speed depends on the temperature at which the process is performed. Isolation of the desired product is effected by means of decomposition of the reaction mixture with water and/or aqueous alkali and separation of the thereal solution by decantation. After distilling-off the solvent, the desired product is purified by distillation in vacuum.

For a better understanding of the present invention some specific Examples are given hereinbelow by way of illustration.

EXAMPLE 1

Into a 0.5 l single-neck flask provided with a magnetic stirrer there are charged 36 g of 3,4-dihydropyrrolo-[1,2-a]-pyrazine, 250 ml of absolute methanol and 1 g of a 10% Pd/BaSO₄. The flask is then connected with the source of hydrogen supply. To remove air, the reaction mass is purged with hydrogen and then allowed to stay in the atmosphere of hydrogen under stirring until the theoretical amount of hydrogen is absorbed. This theoretical amount of hydrogen is absorbed for 3 hours. As a result, the reaction mixture is obtained, wherefrom the catalyst is withdrawn by filtration. From the filtrate the solvent is distilled-off, the residue is distilled in vacuum collecting the fraction with the boiling point of 100°–101° C./7 mm Hg. The yield of 1,2,3,4-tetrahydropyrrolo-[1,2-a]-pyrazine is 34 g (95% of the theory), $n_D^{20}$ is 1.5530. Found, %: C 68.49; H 8.15; $C_7H_{10}N_2$. Calculated, %: C 68.82; H 8.25.

Maleate is prepared by combining solutions of the resulting product and maleic acid (in the molar ratio of 1:1.1 respectively) in ethanol. Melting point is 151°–152° C. (from aqueous ethanol). Found, %: C 55.50; H 6.04; N 11.87. $C_{11}H_{14}N_2O_4$. Calculated, %: C 55.46; H 5.92; N 11.76.

EXAMPLE 2

Into a 50 ml one-neck flask provided with a magnetic stirrer there are charged 2.4 g of 3,4-dihydropyrrolo-[1,2-a]-pyrazine, 20 ml of ethanol and 0.2 g of platinum oxide. Further stages of the process of reduction and recovery of the desired product are performed following the procedure described in the foregoing Example 1. The theoretical amount of hydrogen is absorbed for one hour.

The yield of the desired product is 2.2 g (92% of the theory). Constants and results of analysis of the thus-prepared compound are similar to those described in Example 1.

EXAMPLE 3

Into a 100 ml two-neck flask provided with a stirrer and a reflux condenser there are charged 6 g of 3,4-dihydropyrrolo-[1,2-a]-pyrazine in 50 ml of ethanol and 5.4 g of potassium boronhydride. The reaction mixture is kept for 6 hours under stirring at room temperature. Then the reaction mass is poured into water and the desired product is extracted with benzene. The solvent is distilled-off, the residue is distilled in vacuum and the fraction with the boiling point of 100°–101° C./7 mm Hg is collected.

The yield is 5.2 g (85% of the theoretical value), $n_D^{20}=1.5525$. The results of analysis of the thus-prepared compound are identic to those for the compound prepared in the foregoing Example 1.

EXAMPLE 4

The desired product is prepared following the procedure of Example 3 hereinabove, except that the reaction mixture is heated at the temperature of 78° C. for 2 hours. The yield of the desired product is 79% of the theoretical value. The constants and results of analysis of the thus-prepared product are identic to those of the compound described in Example 1 hereinbefore.

EXAMPLE 5

Into a three-neck 250 ml flask provided with a stirrer reflux condenser and a dropping funnel there are charged 2.28 g of lithium alumohydride in 50 ml of absolute diethyl ether and then a solution of 3.6 g of 3,4-dihydropyrrolo[1,2-a]-pyrazine in 50 ml of absolute diethyl ether are drop-wide added thereto. The reaction mixture is stirred for 4 hours at room temperature and then successively added with 2.3 ml of water, 1.7 ml of a 40% caustic soda and 8 ml of water. The ethereal solution is separated by decantation. The ether is distilled-off, the residue is evaporated with benzene and distilled in vacuum and the fraction with the boiling point of 100°–101° C./7 mm Hg is collected.

The yield is 3.2 g (87% of the theoretical value), $n_D^{22}=1.5522$. The results of analysis of the thus-prepared compound are similar to those for the compound described in Example 1 hereinbefore.

EXAMPLE 6

The desired product is prepared following the procedure of the foregoing Example 5, except that the reaction mixture is heated at reflux at the temperature of 36° C. for one hour. The yield of the desired product is 83% of the theoretical value. The constants and results of analysis of the thus-prepared compound are identic to those for the compound described in Example 1 hereinabove.

What is claimed is:

1. 1,2,3,4-Tetrahydropyrrolo-[1,2-a]-pyrazine of the formula:

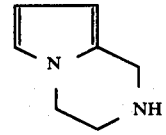

* * * * *